(12) United States Patent
Robinson et al.

(10) Patent No.: US 6,300,140 B1
(45) Date of Patent: Oct. 9, 2001

(54) RAPID TEST EMPLOYING AN ADHESIVE SLIDE

(75) Inventors: Howard N. Robinson, Lutherville; Francisco A. Tausk, Baltimore; Bruce S. Bochner, Lutherville; Neil F. Martin, Potomac, all of MD (US)

(73) Assignee: Leonard Bloom, Towson, MD (US); a part interest (*) Notice: Subject to any disclaimer, the term of this patent is extended or adjusted under 35 U.S.C. 154(b) by 0 days.

(21) Appl. No.: 09/348,524

(22) Filed: Jul. 7, 1999

Related U.S. Application Data

(63) Continuation-in-part of application No. 08/940,404, filed on Oct. 1, 1997, now Pat. No. 5,994,149.

(51) Int. Cl.$^7$ .................................. G01N 33/543
(52) U.S. Cl. .......................... 436/518; 422/55; 422/57; 435/7.1; 435/7.2; 435/7.31; 435/7.36; 435/40.51; 435/962; 435/970; 435/973; 435/921; 435/922; 435/923; 435/924; 435/288.3; 436/528; 436/531; 436/527; 436/809; 436/810
(58) Field of Search .................. 422/55, 57; 435/7.1, 435/7.2, 7.31, 7.36, 40.51, 962, 970, 973, 921, 922, 923, 924, 288.3; 436/518, 531, 528, 527, 809, 810

(56) References Cited

U.S. PATENT DOCUMENTS

| 4,281,061 | 7/1981 | Zuk et al. . |
| 4,424,279 | 1/1984 | Bohn et al. . |
| 4,582,791 | 4/1986 | Khanna et al. . |
| 4,591,570 | 5/1986 | Chang . |
| 5,063,026 | 11/1991 | Wong . |
| 5,128,241 | 7/1992 | Imai et al. . |
| 5,223,405 | 6/1993 | Howell et al. . |
| 5,275,955 | * 1/1994 | Bischoff et al. .................. 436/86 |
| 5,411,894 | * 5/1995 | Cotter et al. .................... 436/174 |
| 5,681,712 | * 10/1997 | Nelson .......................... 435/30 |

OTHER PUBLICATIONS

Journal of American Academy of DERMATOLOGY, Jul. 1997, vol. 37, No. 1.

* cited by examiner

*Primary Examiner*—Christopher L. Chin
(74) *Attorney, Agent, or Firm*—Leonard Bloom

(57) ABSTRACT

A slide having a portion thereof provided with transparent adhesive which adheres to a test sample. The slide and adhesive may be transparent. Specific types of infection and particularly fungal infections can be detected in the test sample using immunotest-methods. In a special embodiment the adhesive slide is fashioned with a peripheral lip or well to contain a test sample and a reagent.

6 Claims, 7 Drawing Sheets

RAPID TEST EMPLOYING AN ADHESIVE SLIDE

RELATED APPLICATIONS

This application is a continuation-in-part of our application Ser. No. 08/940,404 filed Oct. 1, 1997 and now U.S. Pat. No. 5,994,149.

FIELD OF THE INVENTION

This invention relates to a method for immunoassay and reagents thereof which are suitable for detecting fungi present on the skin. Also contemplated are immunoassays for other antigens of pathogenic microorganisms.

BACKGROUND OF THE INVENTION

Physicians are constantly being confronted with situations where the differential diagnosis is between a primary dermatitis such as eczema, psoriasis, seborrheic dermatitis, versus a fungal pathogen such as dermatophytosis or candidiasis of the skin.

Currently, the preferred method of diagnosing a fungal pathogen is a potassium hydroxide wet mount (KOH), and or a fungal culture or screen. The KOH is highly technical and experience-dependent and a fungal screen or culture takes approximately 7 to 30 days for a definitive answer. The KOH wet mount has been combined with DMSO in ranges of 10 to 20 percent to enhance the breakdown of cell walls so that fungal hyphae can be more readily discerned via microscopic identification. There also has been the use of tissue dyes, such as india ink to highlight the hyphael structures for quicker identification. The problem with the above microscopic KOH (with and without DMSO or tissue dye) techniques is that they are dependent upon the individual expertise of the operator. In this scenario there could be a large margin of error both in the over identification of fungi-false positives, and in the under identification of fungi-false negatives. The rate of false positives and false negatives is purely a correlation of operator experience. For example, a board certified dermatologist should predictably have a high rate of specificity, over 90 percent, due to the rigorous training and testing specifically for diseases of the skin. However, a family physician who has limited training and limited experience in skin diseases will predictably have a higher error rate in either over or under detection of the fungi. Therefore, it would be desirable to have a test kit that would eliminate operator error, and have a predictably accurate and reproducible rate of identification of pathogenic fungi, yeasts and molds. The herein disclosed invention is directed to this end.

PRIOR ART PATENTS

Zuk in U.S. Pat. No. 4,281,061 discloses an immunoassay method in which various signals are discussed. The assay can detect an analyte in a concentration of $10^{-4}$ to $10^{-15}$M. Further, the assay can be used to detect microorganisms which may be either intact or lysed.

Khanna in U.S. Pat. No. 4,582,791 discloses immunoassays in which whole cells are detected. Examples of the cells detected are virus infected cells, bacteria and fungi.

None of the prior art patents discloses the invention herein disclosed.

SUMMARY OF THE INVENTION

Treatment regimens that are available for fungal infections of the skin, hair and or nails are targeted for groups of organisms in three broad categories, i.e., dermatophtyes, candidal organisms and/or molds.

Therefore, the clinician only needs to know whether the fungus is a dermatophyte, candidal organism or a mold. It is not necessary to know the exact genus and species of the organism infecting the skin, hair or nails, but the general group category, i.e. dermatophyte—which comprises such organisms as *Trichophyton tonsurans, Microsporum audouinii, Trichophyton violaceum, Trichophyton mentagrophytes, Microsporum canis, Epidermophyton floccosum, Trichophyton concentricum, Microsporum ferrugineum, Microsporum rivalierii, Trichophyton rubrum, Trichophyton megninic and Trichophyton schoenleinii* (the majority but not all inclusive); candida—which comprises such organisms as (but not limited to)—*Candida albicans, Candida krusei, Candida stellatoidea, Candida tropicalis, Candida pseudotropicalis and Candida guillermondii;* and molds—which comprises such organisms (but not limited to)—Aspergillus, Cephalosporium, *Fusarium oxysporum* and *Scopulariopsis brevicalis.*

The invention is directed to a rapid dermatophyte, candidal and mold test kit that will identify the class of organisms infecting the skin, hair and/or nails of humans and animals. This kit will employ polyclonal antibodies to the classes of organisms, not the individual organisms. The rapid identification of the class of organisms either dermatophyte, candidal or mold will immediately allow the clinician to provide the necessary treatment on the day of the patient's visit. All therapies are geared toward classes of organisms, hence, the novel kit employing polyclonal antibodies.

This form of collection would be especially rapid and useful for the entire integument and would provide sufficient antigen to react with a polyclonal antibody to the dermatophtyes. The antibody would be tagged with colored microscopic beads, which in turn could be rapidly and reproducibly identified by any operator physician or allied health professional. The colored microscopic beads attached to each specific antibody could be color coded for each class of organism that the operator is trying to identify, such as a dermatophtyes colored red, candida colored yellow and molds colored green.

It is further anticipated that polyclonal or monoclonal antibody kits could be employed to identify agricultural pathogens, i.e. molds in the field, without waiting for laboratory confirmation.

It is further anticipated that a kit could be employed for home testing in the field of allergy and allergy testing to identify potential substances implicated in allergen-induced asthma and upper respiratory disease. The invention can be directed to the field of allergy and allergy testing and treatment recommendations that would occur after triggering allergens were discovered in the patient's home or work environment.

Tinea is a common disease that affects humans as well as domestic animals. It is produced by pathogenic fungi that colonize the skin. Until now, the methods that the clinician had available for the detection of such pathogens consisted of:

a) submitting samples of scrapings obtained from the skin to a specialized laboratory for culturing, b) direct visualization of scrapings obtained from the skin under a microscope or c) depositing skin or nail scrapings in a flask containing fungal culture material, which change color after about 1 to 2 weeks in the presence of fungi.

These three methods pose disadvantages. For example, the culture of skin is specific and highly sensitive, but usually takes approximately one to four weeks to obtain an answer, and requires the sample be sent to a specialized laboratory. Visualization under a microscope requires the steps of harvesting skin scales; incubating them briefly with warm potassium hydroxide and the slide is then warmed and a coverslip applied. This method takes about 5 minutes, but it requires a trained professional examining the sample, since it is difficult to differentiate fungal hyphae from artifacts such as cell borders, impurities, cloth threads or hairs.

The herein disclosed invention represent novel diagnostic kits for the identification of pathogens that currently take days to weeks to diagnose. These diagnostic kits will find immediate use in their respective fields.

The inventors envision the kit for carrying out the immunoassay of this invention. would contain therein:

1) an adhesive slide,
2) a file or sandpaper, and
3) a container or containers having therein specific antibodies to the various infective agents to be tested for.

Slides with an adhesive surface to capture a skin sample for analysis under a microscope are known in the art. (Dockerty et al, Genitourinary Med. Vol. 71 (1995 pages 407–409). However, the inventors are not aware of the use of a transparent adhesive area on a transparent slide for immuno-testing a sample. The adhesive slide of this invention can be designed with an adhesive surface within a peripheral lip to obtain a sample from the skin or other surface which has to be sampled. Then an immuno-reagent or other reagent can be added to accomplish the reaction. After the immuno-reaction has taken place, the sample can be examined under a microscope to determine whether a reaction has taken place. It is obvious to the worker skilled in the art that the sample could be examined using a cover slip or without a cover slip for the slide. In certain cases a simple magnifying glass can be used to determine whether or not a reaction has taken place.

In many instances, the sample to be tested can be simply lifted from the infected area without pre-preparation, however, at other times it may be advisable to use an abrasive file or sandpaper to loosen the sample so that the loosened sample can be lifted by adhesive on the slide; or alternatively, the loosened sample can be brushed onto the adhesive of the slide. In still another way of obtaining a sample, the sample can be lifted by means of a scalpel and the sample placed on the adhesive slide.

The sample for immuno testing can be obtained from the hair. This is true where the infection affects the scalp. The sample is obtained by plucking the hair and then applying the hair root to the adhesive on the slide for testing.

In its broadest aspect, this invention involves a test slide, for obtaining a sample for testing, comprising a transparent slide provided with a transparent adhesive surface member capable of securing on said adhesive surface a test sample. Also involved in the invention is a method for obtaining a sample for testing, e.g., fungi, molds or allergens, comprising applying to and contacting an area desired to be tested with an adhesive surface member attached to a transparent slide to thereby obtain a sample for testing which has adhered to said adhesive. Immunoassay is one method of assay which can be used in the methods of this invention. The assay can involve a color change which can be viewed under a microscope.

While the herein described invention is principally directed to identifying fungal infections infecting the skin, the invention also envisions identifying inflammations, allergies and other skin infections. Among the skin infections which may be identified are infections caused by molds, bacteria, virus and parasites, etc., infecting man, animal and plants.

OBJECTS

A main object of this invention is to provide a rapid test detecting fungal infections.

A further object of this invention is to provide a means for rapidly obtaining a sample for testing.

A significant object of this method is to produce a device which allows for the easy obtaining of a sample for testing and the rapid obtaining of a test result.

It is the object of this invention to provide a method for a rapid and simplified testing procedure which can qualitatively and quantitatively determine the presence of dermatophtyes on skin.

It is another object of this invention to provide methods in accordance with the preceding object which can be carried out by relatively untrained personnel.

Another object of this intention is to provide an immunoassay method and immunoassay kit that will allow high sensitivity in the detection of fungi.

These and other objects of the present invention will become apparent from a reading of the following specification. In a preferred embodiment 1. The skin to be tested is gently brushed with a gauze to avoid collecting large aggregates of skin scales.
2. A glass or plastic slide containing a two-sided adhesive thin plastic disc on an end is gently applied against the surface of the skin to be tested.
3. The slide is then briefly immersed in potassium hydroxide dissolved in water or dimethylsulfoxide. Alternatively, acetone could be used.
4. The slide is then gently rinsed in water or running water.
5. It is then incubated in a solution containing colored microspheres (polystyrene or plastic beads or liposomes) which have been reacted in such a way that they are coated with high affinity antibodies (polyclonal) that have been raised against the fungal antigens. This can be done by adding 5 drops of a bottle containing the microspheres or alternatively by submerging the part of the slide to be tested in a container that contains the suspension of microspheres. The microspheres will be present in a concentration ranging from between 0.1 and 10%.
6. After 3 minutes the slide is rinsed in water, and examined with a light microscope. Three minutes is a preferred time, but the reaction could take between 3 and 20 minutes or somewhat longer.
7. If the fungi are present, they will become evident by the adherence of the colored microspheres which will render them colored.

MATERIALS AND REAGENTS a) Adhesive material: The inventors propose to utilize a high quality plastic adherent disk such as that manufactured by CuDerm Corporation (D-Squame®). Both sides will contain the adhesive. The disk will be between 0.5 and 1.5 cm in diameter. In employing the method of this invention, the adhesive disc is applied to the affected area of the skin and about 1 microgram to 2–3 grams (and preferably 1 microgram to 1 gram) of material from the affected area is removed and employed in the test.

b) Slide: The inventors propose to utilize clear glass or a clear plastic slide. The adherent plastic disk will be glued on one end of such slide, exposing an adherent surface to the exterior, which until time to use will be protected by a plastic cover as found on the D-Squame product. Surrounding the disk will be a thin rim formed by a substance such as paint or plastic to form a peripheral lip or well which will give the property of forming a "well or moat" which will allow reagents to be added without their running off the slide (thus localizing the reagents, to economize their use). While preferred embodiments of this invention contemplate a transparent slide and adhesive disc, the disc and/or slide may be opaque or translucent. A white slide with transparent adhesive could be useful. The adhesive disc may be replaced with adhesive carriers of various configuration. Clear adhesive is preferred; less than clear adhesive could interfere with the test results. Moreover, the adhesive could be applied directly to the slide surface or can be applied by an adhesive carrier such as a disc. The same adhesive used on the disc can be applied directly to the slide without the need for using a disc.

c) Colored microspheres will be either:

I) Colored microbeads made of polystyrene which are reacted in such a manner that they can become coated with substances such as antibodies on their surface. These can be of a size of between 0.01 micron and 5 microns. These can be purchased from Polysciences, Inc. Besides colored microbeads, the inventors envision using gold particles, such as colloidal gold.

Or:

II) Color enclosed liposomes that have been coated with the appropriate antibodies. Assays involving liposomes are conventional in the art.

d) Antibodies: Polyclonal antibodies will be raised by methods well known to the art. Alternatively, one may use monoclonal antibodies. The antibodies will be directed against antigens found on the fungi or other organisms to be tested. Purification of these will be done as described in the literature. Antigens may be prepared in a natural fashion, or be denatured prior to injection into the animal. The herein disclosed invention contemplates not only a single antibody to detect a fungal antigen, but the invention envisions monoclonal, polyclonal or a mixture of monoclonal antibodies to detect a fungal epitope. Antibodies to detect various fungal epitopes are commercially available and are well known in the art.

e) Reactive microspheres: The antibodies will be attached to the microspheres according to manufacturers instructions, utilizing methods well known to the art. Alternatively, the microspheres may be coated with antibodies that recognize goat IgG, and subsequently these are reacted with antibodies raised in goats against the antigens of interest. Similarly, this could be done with rabbits or other animals. Similarly, the microspheres may be coated with substances such as avidin or streptavidin, and the antibodies conjugated to biotin, or vice-versa.

f) The microspheres may be of different colors, and each color attached to antigens of a particular organism. Each color microsphere may be contained in different containers or alternatively they may be in one container, with a suspension of a mixture of the different microspheres in such a way that each colored sphere will recognize a different organism in the tissue, and a physician or nurse or technician could evaluate for different organisms simultaneously. Gold particles as a tag could be used.

g) Microsphere suspension: The final suspension of spheres will be of a range between 0.1% and 10%, in a solution consisting of sodium chloride in a concentration ranging between 0.1 and 1%, containing a 1% dilution of normal goat serum (to decrease the non-specific binding of beads to the tissue) and a preservative which can be sodium azide, thimerosal, or some other.

DESCRIPTION OF THE DRAWINGS

FIG. 15 is a cross section taken along lines 15—15 of FIG. 14. The dashed lines represent the flexible well pushed in.

In the figures the adhesive surface has not been shown as a separate layer for ease of illustration.

DESCRIPTION OF THE PREFERRED EMBODIMENTS

Figure 1:
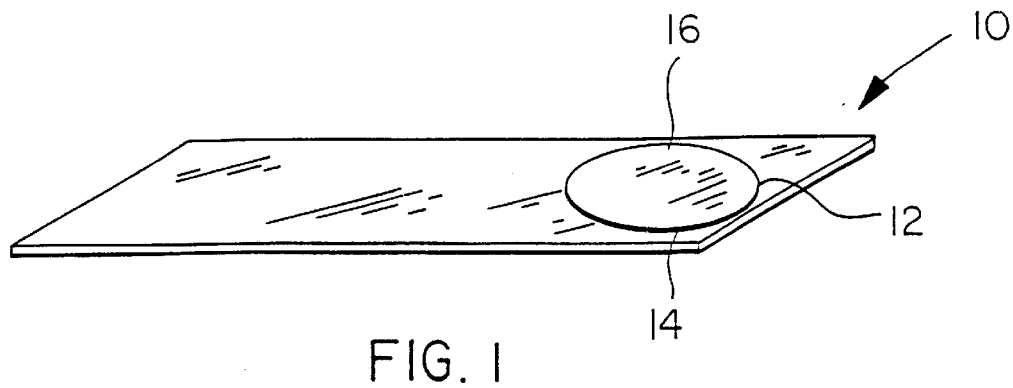
FIG. 1 is a perspective view of the transparent slide with adhesive surface area covered by a plastic cover.
Figure 2:
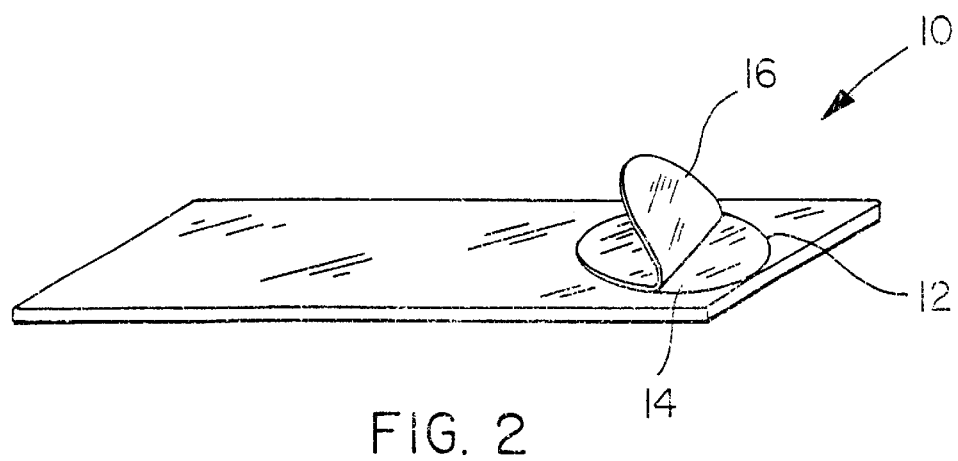
FIG. 2 is a perspective view of the transparent slide with the plastic cover partially removed from the adhesive surface.
Figure 3:
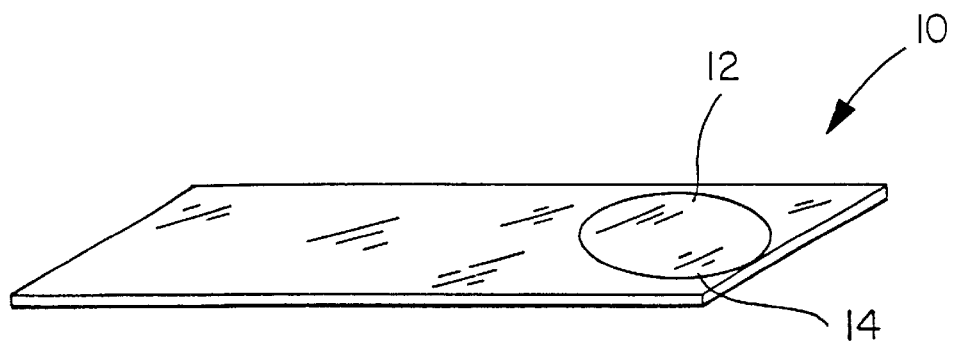
FIG. 3 is a perspective view thereof with the plastic cover fully removed from the adhesive surface.
Figure 4:
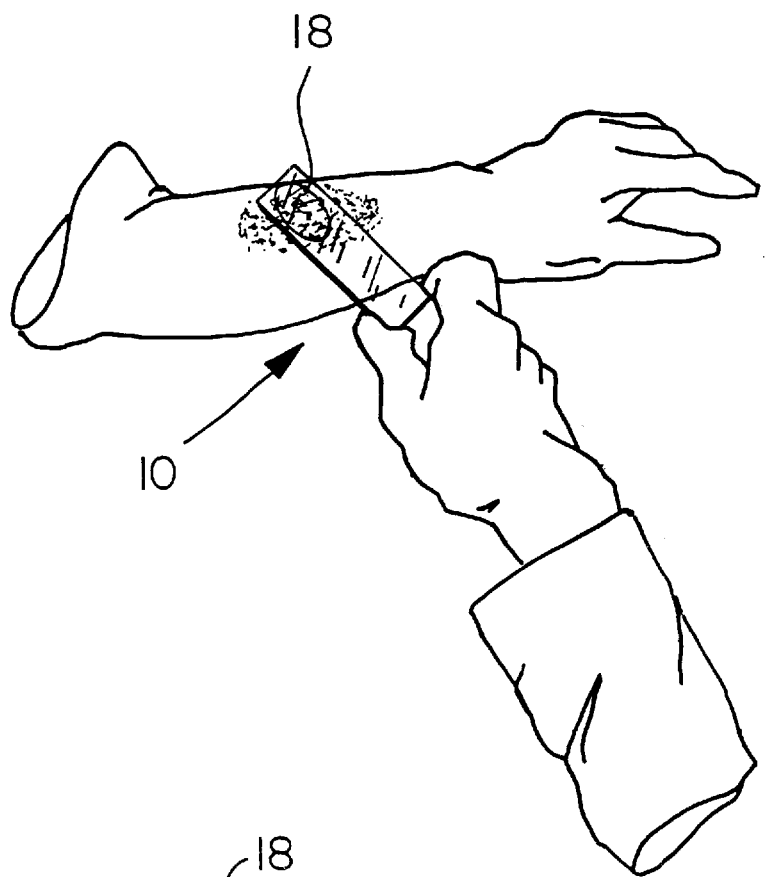
FIG. 4 is a view of the adhesive surface on the transparent slide applied to an infected area of the skin.
Figure 5:
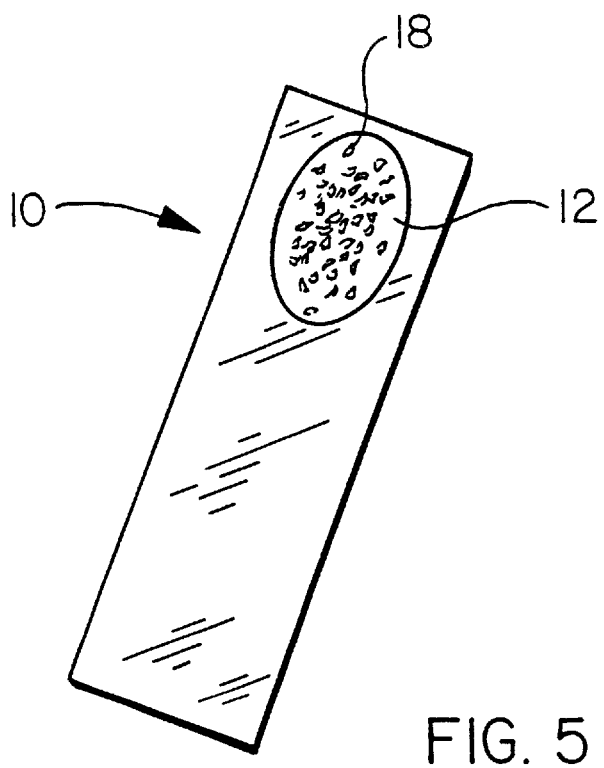
FIG. 5 is a view of the transparent slide with sample attached to the adhesive surface.
Figure 6:
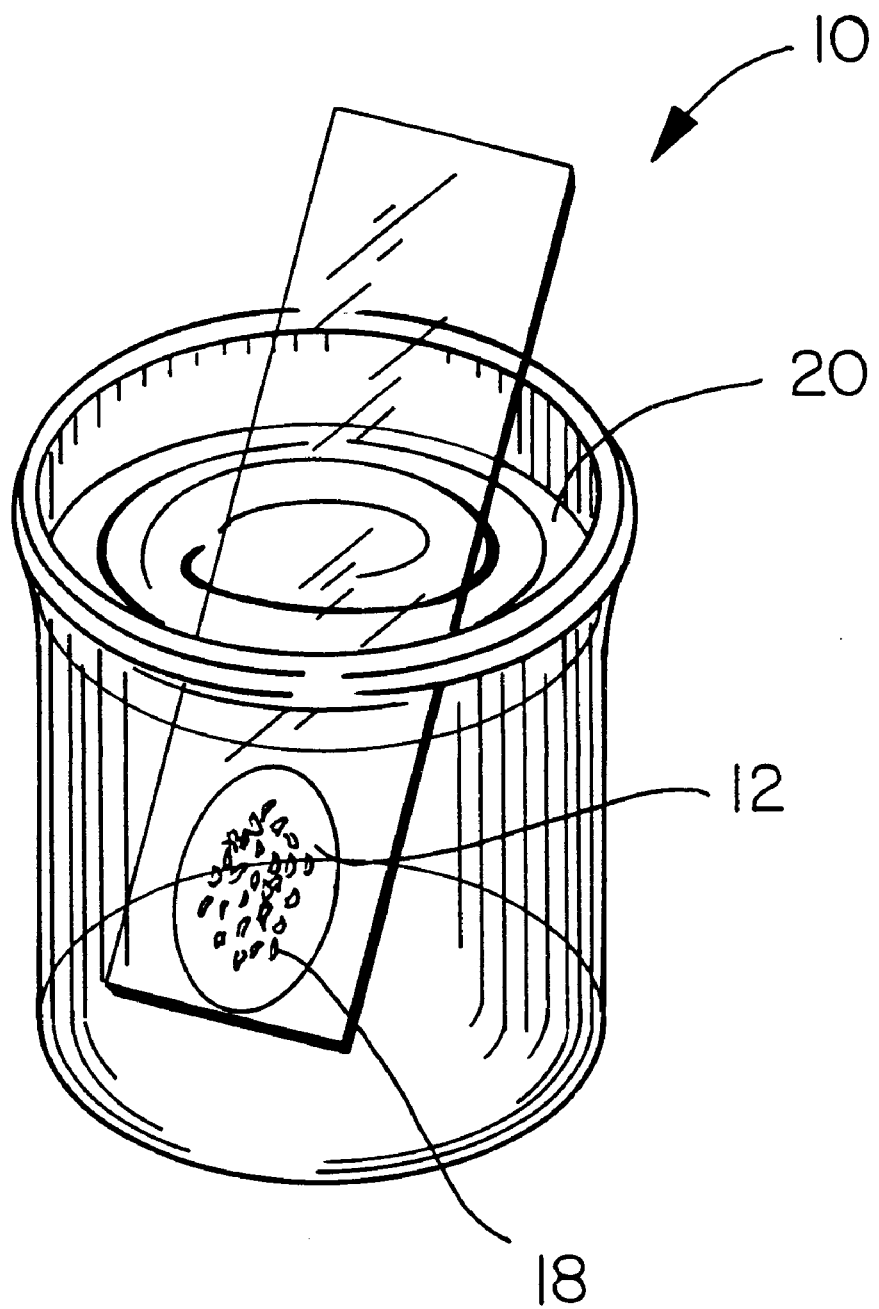
FIG. 6 is a view of the sample on the adhesive surface being applied to a test solution.
Figure 7:
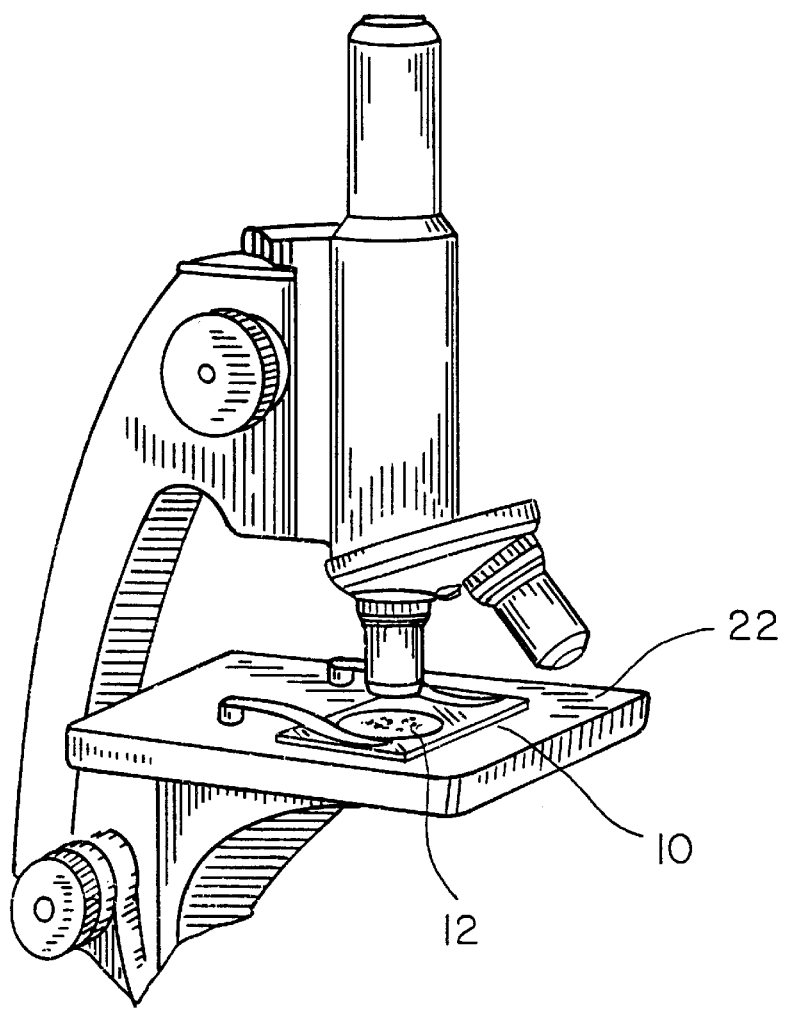
FIG. 7 is a view of the transparent slide with the adhesive surface containing the test analyte for examination under the microscope.

Referring to FIGS. 1–7, a transparent slide 10 has an adhesive surface area 12 for receiving a test sample on the surface thereof. The transparent analytic slide 10 has mounted on its top plannar surface a transparent adhesive disc 14 (FIGS. 1 and 2). The adhesive disc 14 prior to use is covered with a peelable cover 16 to protect the adhesive from soiling (FIG. 2). In use the peelable cover 16 is removed to expose the adhesive surface 12 (FIG. 3). The adhesive surface 12 is applied to an infected skin surface to lift off particles 18 of the infected surface (FIGS. 4 and 5). The adhesive area 12 of the slide 10 with particles 18 of analyte attached thereto are applied to the test solution 20 to cause the analyte to react with the test solution (FIG. 6). Once the test reaction is complete, the reacted analyte can be viewed under the microscope 22 to see whether a reaction has taken place and/or the type of reaction which has taken place (FIG. 7).

Figure 8:
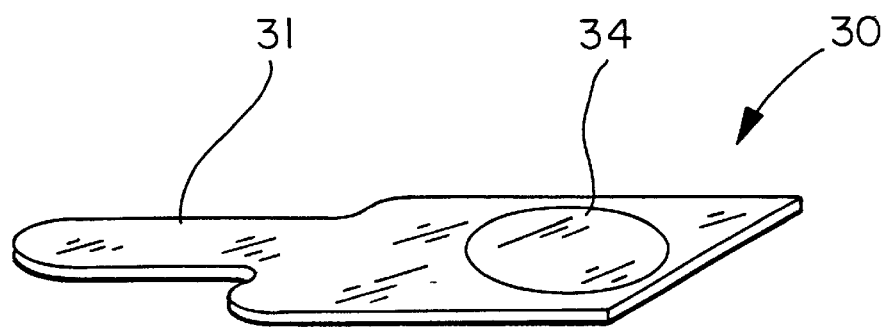
FIG. 8 is a view illustrating a slide with a handle.

In an alternative embodiment of this invention 30 (FIG. 8) the slide with adhesive disc 34 thereon has an attached handle 31.

Figure 9:
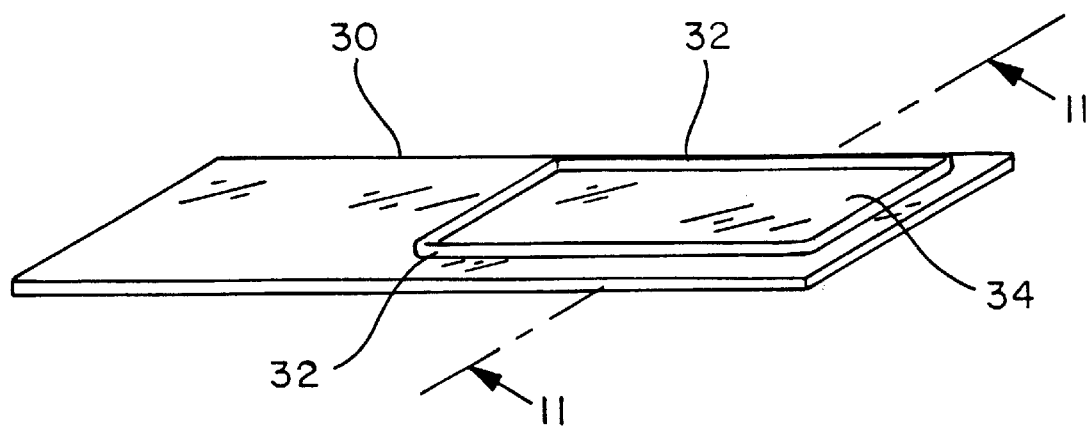
FIG. 9 is a perspective view of a slide with peripheral lip.
Figure 10:
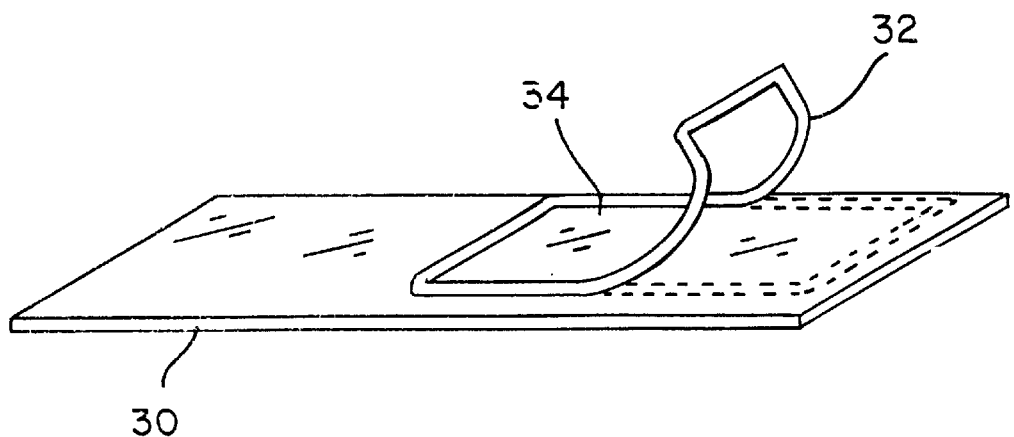
FIG. 10 is a view illustrating the peripheral lip being removed.
Figure 11:
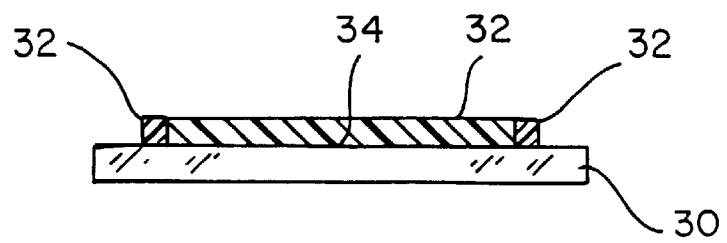
FIG. 11 is a cross-section thereof taken along lines 11—11 of FIG. 9. The dashed lines represent the original position of the peripheral lip.
Figure 12:
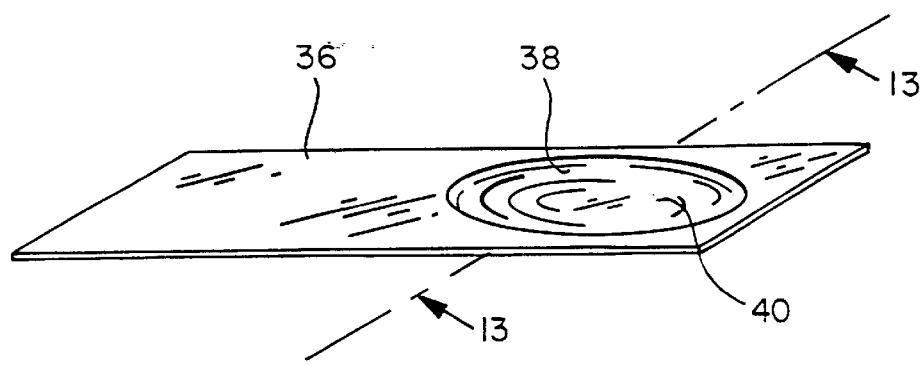
FIG. 12 is a perspective view of a slide with a well.
Figure 13:
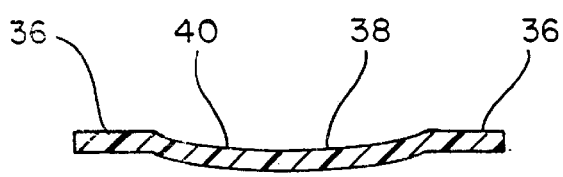
FIG. 13 is a cross-section thereof taken along lines 13—13 of FIG. 12.

Special embodiments of this invention are described in FIGS. 9–13. The slide 30 in FIGS. 9–11 has a peripheral lip 32 and clear adhesive 34 disposed therein. In use the adhesive area 34 of the slide 30 is applied to the surface area to be tested to gather a sample. The peripheral lip 32 is integrally attached to the slide allows for reagent to be applied within the peripheral lip to the slide 30 for obtaining a test result visible to the naked eye under a microscope or with a magnifying glass. This embodiment is shown in FIG. 9 and in cross-section in FIG. 11. The peripheral lip 32 could be covered with a cover slip for viewing the sample. An alternative embodiment (FIG. 10) envisions the peripheral lip 32 removably mounted on the slide so that a cover slip could be placed over the reacted sample for better focus in microscopic viewing.

Figure 15:
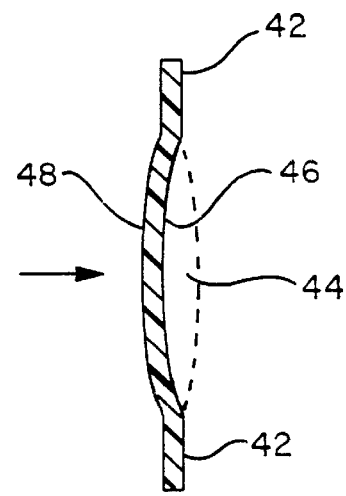
Figure 14:
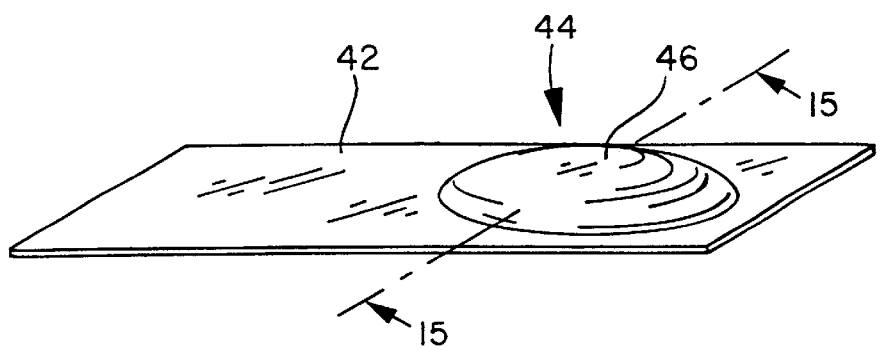
FIG. 14 is a view illustrating a slide with a flexible well.

In another elegant embodiment (FIGS. 12–13) of this invention a slide 36 has a well 38 having adhesive 40 therein. The well 38 can be shallow so as to be able to pick up a sample for testing or the well could be deeper and flexible (FIGS. 14–15). Referring to FIGS. 14–15, an embodiment of the slide 36–42 with well 44 envisions the slide 42 and well 44 being made of flexible material such as plastic. In use, the concave portion 46 of the well 44 is placed over the area to be tested. The convex area 48 of the well 44 is pressed down over the test area and the test sample is adhered to the adhesive portion of the well. After being pressed down over the test area, the well, since it is flexible, returns to its natural relaxed shape (FIG. 14–15). Once the well is in its natural shape (FIG. 14) the slide is turned over and reagent added to the well for reaction with the test sample. Once the reaction is complete, the sample can be viewed with the naked eye, with a magnifying glass or under the microscope to determine the outcome of the test.

The advantage of the flexible well is that the well can be made deeper to allow for the use of a larger amount of test reagent.

The convex surface of the well, alternatively, may have a flattened center to facilitate microscopy focusing.

Figure 16:
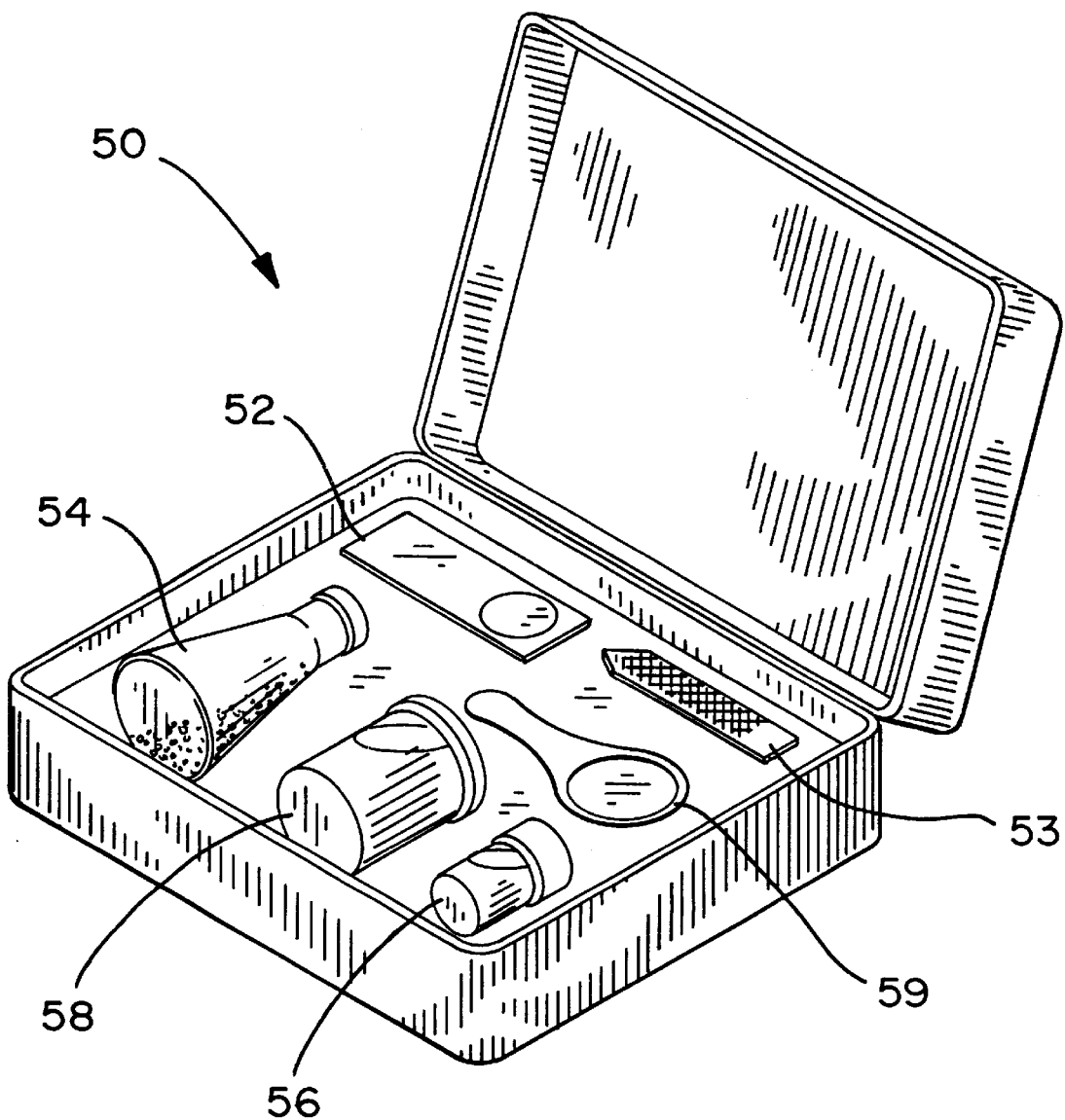
FIG. 16 is a view illustrating a kit with components useful in carrying out the rapid test of this invention.

With reference to FIG. 16, the inventors envision supplying a kit 50 to be used in carrying out the methods of this invention. The kit 50 would contain the adhesive slide 52 for obtaining the sample. In addition, as an optional feature, the kit would contain a file 53 or sandpaper which could be used to loosen a surface sample before applying the adhesive slide 52 to the sample. A container of antibody sensitized colored microbeadlets 54 would be included. Exemplary of the sensitized colored microbeadlets would be red colored microbeadlets sensitized to dermatophytes, yellow colored microbeadlets sensitized to candida and green colored microbeadlets sensitized to mold. It is to be understood that liposomes could be used for immunoassay. A container 56 containing acetone, potassium hydroxide solution or dimethylsulfoxide would be provided for washing the slide. A small beaker 58 could be supplied in which to carry out the reaction. A magnifying glass 59 is provided in the kit for aid in better viewing to determine if a reaction has taken place. In place of a magnifying glass, it may be feasible to determine if a reaction has taken place using a microscope. In the kit the microbeads are to be supplied in a suspension or in dry form to which pure water is to be added to form a suspension.

The adhesive slide of this invention can be used to detect an infinite number of plant and crop infections and, particularly, fungal infections.

Monoclonal and polyclonal antibodies would be useful for the diagnosis of various fungal infections of plants, especially various food crops. Fungi affect important grain, bean and vegetable crops with a significant economic impact. Estimates of annual loss of wheat due to disease range from 10 to 20%. (McGraw—Hill Encyclopedia of Science and Technology, 7$^{th}$ Edition, N.Y., 1992, McGraw—Hill, 458–9). The following list correlates a few crops with some common fungal pathogens.

Wheat

1) *Puccinia graminis f. sp. tritici* causes black stem rust.

2) *Puccinia reconditia* causes leaf rust.

3) *Ustilago nuda* causes loose smut.

Corn

More than 100 diseases of corn are known worldwide. Worldwide reduction in grain production is estimated to average 9% and in the Corn Belt (of the U.S.C.) to average 7–17%. Diseases are caused by bacteria, fungi, nematodes, viruses and mycoplasma. Important fungal diseases are as follows:

1) Seedling diseases—Diplodia, Fusarium, Penicillium and Pythium cause seed decay and seedling blight.

2) Leaf diseases
   a) *Helminthosporidum maydis* causes southern corn leaf blight.

Soybeans

Annual loses from diseases are estimated at 12%. Fungi cause more diseases than other parasitic organisms. Some important fungal infections are:

1) *Peronospora manshuria* causes mildew, a leaf spotting disease.

2) *Septoria glycines* causes brown spot.

3) *Corynespora cassiicola* causes target spot.

Many diseases which affect fruit and vegetable plants are caused by fungi. The following are some more common examples:

1) Anthachose affects beans (lima and snap), blackberries, cucumbers, mint, muskmelons, peppers, pumpkins, raspberries, rhubarb, squash, tomatoes and watermelons.

2) Apple scab affects apples and pears.

3) Asparagus rust affects asparagus.

4) Bean rust affects lima and snap beans.

The samples can be obtained from the plant by simply applying the adhesive to the infected area of the plant or the adhesive could be placed over loose scrapings or filings to obtain a sample onto the adhesive.

The adhesive slide of this invention could also be employed to detect microbial keratitis which is a potentially blinding corneal infection caused by bacteria, fungi or parasites. In detecting corneal infections, a small amount of material from a corneal scraping would be applied to adhesive on the slide and then subjected to immuno-testing and visualization.

The surface to be tested with the adhesive slide may be an inert surface suspected of containing an allergen; such as surfaces found in the home or in industry.

The adhesive slide of this invention could be used to gather a sample from fungal infected finger nails or toe nails. The adhesive slide could be used after filing the fungal-infected finger nail or toe nail and dropping the filings onto an adhesive slide or the adhesive slide could be placed over the loose filings from the nails and thus gathered. After this procedure the sample on the adhesive can be tested.

Advantage of the method

The novel methods of this invention allow for fungal evaluation to be performed by unskilled personnel in a rapid fashion, in such a way that the physician may obtain confirmation of fungal elements in a short period of time.

This method allows physicians and technicians who are not specifically trained in the art of fungal evaluation to perform the test accurately.

This method allows for a clear distinction between different organisms which would require different treatments. The test applies to dermatophtyes, candida, other yeasts and molds, and can be utilized in a similar fashion for the detection of skin parasites such as scabies and pinworms and in agriculture to detect pathogens such as molds. While the herein described invention is directed primarily to identifying infections occurring in humans, it is also useful in identifying infections in animals such as mammals, amphibians and fish, and also in plants.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A test slide for obtaining a sample for testing comprising a slide being provided with an adhesive surface capable of securing on said adhesive surface a test sample, and wherein the adhesive surface is contained within a removable peripheral lip.

2. The test slide for obtaining a sample for testing of claim 1 wherein the slide is transparent and the adhesive surface is transparent.

3. The test slide of claim 2 wherein a peripheral lip surrounds the adhesive surface so that test reagent can be applied to the adhered sample without running off.

4. The test slide of claim 1 having a handle disposed thereon for ease of handling.

5. A test slide for obtaining a sample for testing comprising a slide being provided with an adhesive surface within a well capable of securing on said adhesive surface a test sample, wherein the well is made of a flexible material such that when the concave portion of said well is placed over a sample to be tested and the well pressed down over the sample, the sample will adhere to the adhesive in the well and when the press is released, the well will return to its unflexed position and will be capable of receiving a reagent for testing the sample.

6. The test slide of claim 5 wherein the well has a flattened center to facilitate microscopy focusing.

* * * * *